United States Patent
Kennedy et al.

(10) Patent No.: US 12,214,067 B2
(45) Date of Patent: Feb. 4, 2025

(54) OIL-IN-WATER EMULSION SUNSCREEN COMPOSITION

(71) Applicant: ISP INVESTMENTS INC., Wilmington, DE (US)

(72) Inventors: Diane M. Kennedy, Bayonne, NJ (US); Donald I. Prettypaul, Englewood, NJ (US); Hani M. Fares, Somerset, NJ (US); Rita Marie Guerrero, Hillsborough, NJ (US)

(73) Assignee: ISP INVESTMENTS INC., Wilmington, DE (US)

( * ) Notice: Subject to any disclaimer, the term of this patent is extended or adjusted under 35 U.S.C. 154(b) by 418 days.

(21) Appl. No.: 15/115,479

(22) PCT Filed: Jan. 30, 2015

(86) PCT No.: PCT/US2015/013689
§ 371 (c)(1),
(2) Date: Jul. 29, 2016

(87) PCT Pub. No.: WO2015/116899
PCT Pub. Date: Aug. 6, 2015

(65) Prior Publication Data
US 2017/0165187 A1 Jun. 15, 2017

Related U.S. Application Data

(60) Provisional application No. 61/934,158, filed on Jan. 31, 2014.

(51) Int. Cl.
| | |
|---|---|
| *A61K 8/35* | (2006.01) |
| *A61K 8/06* | (2006.01) |
| *A61K 8/37* | (2006.01) |
| *A61K 8/40* | (2006.01) |
| *A61K 8/60* | (2006.01) |
| *A61K 8/81* | (2006.01) |
| *A61Q 17/04* | (2006.01) |

(52) U.S. Cl.
CPC ............ *A61K 8/8182* (2013.01); *A61K 8/062* (2013.01); *A61K 8/35* (2013.01); *A61K 8/37* (2013.01); *A61K 8/375* (2013.01); *A61K 8/40* (2013.01); *A61K 8/604* (2013.01); *A61Q 17/04* (2013.01); *A61K 2800/30* (2013.01); *A61K 2800/596* (2013.01)

(58) Field of Classification Search
CPC ........ A61K 8/8182; A61K 8/062; A61K 8/35; A61K 8/37; A61K 8/375; A61K 8/40; A61K 8/604; A61K 2800/30; A61K 2800/596; A61Q 17/04
See application file for complete search history.

(56) References Cited

U.S. PATENT DOCUMENTS

| | | | | |
|---|---|---|---|---|
| 4,917,883 | A * | 4/1990 | Strobridge | A61K 8/06 404/60 |
| 5,730,993 | A * | 3/1998 | Allard | A61K 8/0204 424/401 |
| 5,733,531 | A * | 3/1998 | Mitchnick | A61K 8/27 424/400 |
| 2001/0022966 | A1* | 9/2001 | Gers-Barlag | A61K 8/29 424/59 |
| 2001/0047039 | A1* | 11/2001 | McManus | A61K 8/0295 516/98 |
| 2003/0049214 | A1 | 3/2003 | Muller | |
| 2003/0059391 | A1* | 3/2003 | L'Alloret | A61K 8/90 424/70.11 |
| 2011/0014139 | A1* | 1/2011 | Viala | A61K 8/87 424/59 |
| 2011/0236498 | A1 | 9/2011 | Marteaux et al. | |
| 2013/0164232 | A1* | 6/2013 | Castro | A61K 8/40 424/60 |

FOREIGN PATENT DOCUMENTS

| | | |
|---|---|---|
| WO | WO2009038710 A2 | 3/2009 |
| WO | WO2012149355 A1 | 11/2012 |

OTHER PUBLICATIONS

International Search Report, PCT/US2015/013689 published on Aug. 6, 2015.

* cited by examiner

*Primary Examiner* — Ali Soroush
(74) *Attorney, Agent, or Firm* — William J. Davis; Nathalie Tietcheu

(57) ABSTRACT

In accordance with the present invention there is provided an oil-in-water emulsion sunscreen composition comprising (a) a UV active, (b) a first emulsifier having an HLB value less than 5 and (c) optionally a second emulsifier having an HLB value greater than 5 present in an amount of less than 0.2% w/w of the composition. The oil-in-water sunscreen composition is characterized by the absence of an emulsifiable polymer and is capable of providing little to no whitening when applied to wet skin.

6 Claims, No Drawings

OIL-IN-WATER EMULSION SUNSCREEN COMPOSITION

FIELD OF THE INVENTION

The present invention relates to an oil-in-water sunscreen composition having the ability to be successfully applied to wet skin without flaking or turning white.

BACKGROUND OF THE INVENTION

Conventional sunscreen products generally take the foiln of UV-filter compounds and/or particulate UV-blocking compounds (collectively "UV actives") that are solubilized, emulsified, or dispersed in a vehicle which is topically applied to the skin. The UV actives, typically through the aid of polymers and other ingredients included in the vehicle, form a thin, protective, and often water-resistant layer on the skin.

While typical sunscreen products are successful at providing a durable protective barrier when applied to dry skin, such is not typically the result when applied to skin that is damp with sweat or with residual water thereon. When applied to wet skin, the tendency of conventional sunscreen products is to dilute the UV actives, smear, form an incomplete film, often one that flakes or peels off the skin, and/or take on an undesired pasty, white appearance. This undesirable whitening is particularly problematic when the composition includes water.

Accordingly, severe aesthetic and performance problems still exist in prior art "wet skin" sunscreen products. Applicants have discovered a new oil-in-water emulsion sunscreen composition that provides consistent and pleasant application to wet skin as well as the ability of the resulting film to protect the skin from damaging ultraviolet radiation.

SUMMARY OF THE INVENTION

In accordance with the present invention there is provided an oil-in-water emulsion sunscreen composition comprising (a) one or more UV actives, (b) a first emulsifier having an HLB value less than 5 and (c) optionally a second emulsifier having an HLB value greater than 5 present in an amount of less than 0.2% w/w of said composition. The oil-in-water sunscreen composition is characterized by the absence of an emulsifiable polymer. The composition is capable of providing little to no whitening when applied to wet skin.

DETAILED DESCRIPTION

Before describing particular embodiments of the invention, it is helpful to define a few terms first as those were used in this description.

The terms "ultraviolet" and "UV" refer to electromagnetic radiation, especially solar electromagnetic radiation, with a wavelength from about 100 nm to about 400 nm, and includes the UV-A and UV-B sub-classifications of such radiation.

The term "UV-A" refers to ultraviolet electromagnetic radiation with a wavelength from about 320 nm to about 400 nm, and includes UV-A1 (from about 340 nm to about 400 nm) and UV-A2 (from about 320 nm to about 340 nm).

The term "UV-B" refers to ultraviolet electromagnetic radiation with a wavelength from about 290 nm to about 320 nm.

The term "sunscreen" refers to personal care and/or pharmaceutical formulations comprising an effective amount of one or more UV-absorbing compounds. Sunscreen formulations include beach and non-beach products that are applied to the face, décolleté, lips, and skin to treat and/or protect against erythema, burns, wrinkles, lentigo ("liver spots"), skin cancers, keratotic lesions, and cellular changes of the skin; and to hair to treat and/or protect against color changes, lack of luster, tangles, split ends, unmanageability, and embrittlement. Other categories of sunscreens that fit into this definition are sun blocks, all-day protection formulas, baby sun care, and tanning preparations that have UV absorber(s).

As used herein an "emulsifier" refers to a compound/composition that aids in the formation of an oil in water, or a water in oil, emulsion.

The present invention relates to an oil-in-water emulsion sunscreen composition comprising (a) one or more UV actives, (b) a first emulsifier having an HLB value less than 5 and (c) optionally a second emulsifier having an HLB value greater than 5 present in an amount of less than 0.2% w/w of said composition, wherein said oil-in-water sunscreen composition is free of emulsifiable polymer.

In accordance with the practice of the present invention emulsifiers having an HLB<5 include:

TABLE 1

| Type | HLB |
|---|---|
| Glycol Distearate | 1 |
| Sorbitan Trioleate | 1.8 |
| Glycol Stearate | 2.9 |
| Sorbitan Sesquioleate | 3.7 |
| Glyceryl Stearate | 3.8 |
| Glyceryl Dilaurate | 4 |
| Lecithin | 4 |
| Sorbitan Oleate | 4.3 |
| Sorbitan Stearate | 4.7 |
| Sorbitan Isostearate | 4.7 |
| Oleth-2 | 4.9 |
| Steareth-2 | 4.9 |

The first emulsifier is present in an amount of 0.1 to 5.0%, preferably 0.2 to 4.0%, and most preferably 0.5 to 2.0% by weight based on the total weight of the composition. One or more first emulsifiers may be present. Preferred first emulsifiers include glyceryl stearate and glyceryl dilaurate.

In accordance with the practice of the present invention, emulsifiers having an HLB>5 include:

TABLE 2

| Type | HLB |
|---|---|
| Calcium Stearoyl Lactylate | 5.1 |
| Glyceryl Laurate | 5.2 |
| Ceteth-2 | 5.3 |
| PEG-30 Dipolyhydroxystearate | 5.5 |
| Glyceryl Stearate SE | 5.8 |
| PEG-4 Dilaurate | 6 |
| Sorbitan Stearate (and) Sucrose Cocoate | 6 |
| Methyl Glucose Sesquistearate | 6.6 |
| PEG-10 Sunflower Glycerides | 8 |
| Sodium Stearoyl Lactylate | 8.3 |
| Sorbitan Laurate | 8.6 |
| PEG-40 Sorbitan Peroleate | 9 |
| Lecithin | 9.7 |
| Laureth-4 | 9.7 |
| PEG-7 Glyceryl Cocoate | 10 |
| PEG-20 Almond Glycerides | 10 |
| Linoleamide DEA | 10 |
| PEG-25 Hydrogenated Castor Oil | 10.8 |
| Cetearyl Glucoside | 11 |
| Sucrose Stearate | 16 |

TABLE 2-continued

| Type | HLB |
|---|---|
| Polysorbate 85 | 11 |
| Glyceryl Stearate (and) PEG-100 Stearate | 11 |
| Stearamide MEA | 11 |
| Oleth-10/Polyoxyl 10 Oleyl Ether NF | 12.4 |
| Oleth-10 | 12.4 |
| Oleth-20 | 12.4 |
| Ceteth-10 | 12.9 |
| PEG-8 Laurate | 13 |
| Cocamide MEA | 13.5 |
| Polysorbate 60 | 14.9 |
| PEG-60 Almond Glycerides | 15 |
| Isosteareth-20 | 15 |
| Lauramide DEA | 15 |
| Sucrose Stearate (D-1816) | 16 |
| Polysorbate 80 | 15 |
| PEG-20 Methyl Glucose Sesquistearate | 15 |
| Ceteareth-20 | 15.2 |
| Oleth-20 | 15.3 |
| Steareth-21 | 15.5 |
| Ceteth-20 | 15.7 |
| Isoceteth-20 | 15.7 |
| Polysorbate 20 | 16.7 |
| Laureth-23 | 16.9 |
| PEG-100 Stearate | 18.8 |
| PEG-80 Sorbitan Laurate | 19.1 |

It is contemplated that one or more of the second emulsifier can be used in combinations. In preferred embodiments, the weight ratio of the second emulsifier to the first emulsifier is less than 0.01, preferably less than 0.002 and more preferably less than 0.001.

The above-described emulsifiers and their corresponding HLB (hydrophilic-lipophilic balance) values are known to those skilled in the art. Further information on HLB can be found in Physical Pharmacy, Third Edition, Physical Chemical Principles in the Pharmaceutical Sciences by Martin et al, pages 452-455.

The sunscreen composition also comprises at least one UV active. Examples of UV actives include: octyl salicylate (2-ethylhexyl salicylate, Escalol® 587); pentyl dimethyl PABA; octyl dimethyl PABA (padimate O, Escalol® 507); benzophenone-1; benzophenone-6 (Uvinul® D-49); 2-(2H-benzotriazole-2-yl)-4,6-di-tert-pentylphenol (Uvinul® 3028); ethyl-2-cyano-3,3-diphenylacrylate (Uvinul® 3035); homomenthyl salicylate (homosalate); bis-ethylhexyloxyphenol methoxyphenyl triazine (bemotrizinol, Escalol® S); methyl-(1.2,2,6,6-pentamethyl-4-piperidyl)-sebacate (Uvinul® 409214); benzenepropanoic acid, 3,5-bis (1,1-dimethyl-ethyl)-4-hydroxy-, C7-C9 branched alkyl esters (Irganox® 1135); 2-(2H-benzotriazole-2-yl)-4-methylphenol (Uvinul® 3033P); diethylhexyl butamido triazone (iscotrizinol, Uvasorb® HEB); amyl dimethyl PABA (lisadimate, glyceryl PABA); 4,6-bis(octylthiomethyl)-o-cresol (Irganox® 1520); CAS number 65447-77-0 (Uvinul® 5062H, Uvinul® 5062GR); red petroleum; ethylhexyl triazone (Uvinul® T-150); octocrylene (Escalol® 597); isoamyl-p-methoxycinnamate (amiloxate, Neo Heliopan® E1000); drometrizole; titanium dioxide; 2,4-di-tert-butyl-6-(5-chloro-21-1-benzotriazole-2-yl)-phenol (Uvinul® 3027); 2-hydroxy-4-octyloxybenzophenone (Uvinul® 3008); benzophenone-2 (Uvinul® D-50); diisopropyl methylcinnamate; PEG-25 PABA;2-(1,1-dimethylethyl)-6- [[3-(1,1-demethylethyl)-2-hydroxy-5 -methylphenyl] methyl-4-methylphenyl acrylate (Irganox® 3052); drometrizole trisiloxane (Mexoryl® XL); menthyl anthranilate (meradimate); bis-(1,2,2,6,6-pentamethyl-4-piperidyl)-sebacate; butyl methoxydibenzoylmethane (avobenzone, Escalol® 517); 2-ethoxyethyl p-methoxycinnamate (cinnoxate); benzylidene camphor sulfonic acid (Mexoryl® SL); dimethoxyphenyl-[1-(3,4)]-4,4-dimethyl1,3-pentanedione; zinc oxide.; N,N'-hexane-1,6-diyl-bis[3-(3,5-di-tert-butyl-4-hydroxyphenylpropionamide)] (Irganox® 1098); pentaerythritol tetrakis[3 -(3, 5-di-tert-butyl-4-hydroxyphenyl)propionate] (Irganox® 1010); 2,6-di-tert-butyl-4-[4,6-bis(octylthio)- 1,3,5-triaziN-2-ylamino] phenol (Irganox® 565); 2-(211-benzotriazole-2-yl)-4,6-bis(1-methyl-1-phenylethyl)phenol (Uvinul® 3034); trolamine salicylate (triethanolamine salicylate); diethylanolamine p-methoxycinnamate (DEA methoxycinnamate); polysilicone-15 (Parsol® SLX); CAS number 152261-33-1(Uvinul® 505014); 4-methylbenzylidene camphor (Eusolex® 6300, Parsol® 5000); bisoctrizole (Tinosorb® M); benzenamine, N-phenyl-, reaction products with 2,4,4-trimethylpentene (Irganox® 50507); sulisobenzone, Escalol® 577); (2-ethylhexyl)-2-cyano-3,3-diphenylacrylate (Uvinul® 3039); digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[(2'-cyano-; bis-(2,2,6,6-tetramethyl-4-piperidyl)-sebacate (Uvinul® 407711); benzophenone-5 (sulisobzone sodium); 1,3,5-tris(3,5-di-tert-butyl-4-hydroxybenzyl)- 1,3,5-triazine-2,4,6(1H,3H, 5H)-trione (Irganox® 3114); hexamethylendiamine (Uvinul® 4050II); benzophenone-8 (dioxybenzone); ethyl-4-bis (hydroxypropyl) aminobenzoate (roxadimate); 6-tert-butyl-2-(5 -chloro-2H-benzotriazole-2-yl)-4-methylphenol (Uvinul® 3026); p-aminobenzoic acid (PABA); 3,3',3",5,5', 5"-hexa-tert-butyl-α-α'-α"-(mesitylene-2,4,6-triyl)tri-p-cresol (Irganox® 1130); lawsone with dihydroxyacetone; benzophenone-9(Uvinul® DS-49); benzophenone-4 (sulisobenzone); ethylhexyl dimethoxy benzylidene dioxoimidazoline propionate; N,N'-bisfoimyl-N,N'-bis-(2,2,6,6-tetramethyl-4-piperidinyl)-; 3-benzylidene camphor (Mexoryl® SD); terephthalylidene dicamphor sulfonic acid; camphor benzalkonium methosulfate (Mexoryl® SO); bisdisulizole disodium (Neo Heliopan® AP); etocrylene; ferulic acid; 2-(2H-benzotriazole-2-yl)-4-(1,1,3,3-tetramethylbutyl)-phenol (Uvinul® 3029); ecamsule (Mexoryl® SX); 4,6-bis(dodecylthiomethyl)-o-cresol (Irganox® 1726); beta-2-glucopyranoxy propyl hydroxy benzophenone; phenylbenzimidazole sulfonic acid (ensulizole, Eusolex® 232, Parsol® HS); benzophenone-3 (oxybenzone, Escalol® 567); diethylamine hydroxybenzoyl hexylbenzoate (Uvinul® A Plus); 3',3'-diphenylacryloyl)oxy]methyl}-propane (Uvinul® 3030); and ethylhexyl p-methoxycinnamate (Escalol® 557).

It is generally desirable to formulate the sunscreen product with more than one UV active. The reasons for such a formulary strategy are many, and include cost, manufacturing, and product performance considerations. Regarding the latter, blends of two or more UV actives may help extend the range of UV radiation absorption provided by the sun-care product, especially to cover the various UV-A and UV-B designations of UV radiation. Through using satisfactory blends, sun-care products can be formulated to provide partial or even complete UV protection.

The UV active or actives can be present in an amount of 0.1 to 50%, preferably 0.5 to 45% and most preferably 1.0 to 40% by weight of the composition.

The oil-in water emulsion sunscreen composition of the invention can be prepared according to techniques known in the art. For example, the oil phase and the aqueous phase can be prepared separately, and thereafter the oil phase can be gradually added to the aqueous phase, followed by emulsification by mixing, stirring or the like.

The water phase is present in an amount of greater than 50% by weight of the composition. The oil phase is present in an amount less than 50% by weight of the composition. In preferred embodiments, the aqueous phase accounts for from 55 to 97% and more preferably 57 to 70% by weight of the composition, and the oil phase accounts for from 3 to 35% and more preferably 7 to 15% by weight of the composition.

The composition must be free of emulsifiable polymers, i.e., polymers containing hydrophobic chains. The reason for this is that emulsifiable polymers cause flaking and/or whitening upon application to wet skin. Examples of common emulsifiable polymers include Pemulen TR-1 and Pemulen TR-2 (acrylates/$C_{10-30}$ alkyacrylates crosspolymer) and Sepigel 305 (polyacrylamide/$C_{13-14}$ isoparaffin/Laureth-7), SEPINOV™ EMT10 (Hydroxyethyl Acrylate/Sodium Acryloyldimethyl Taurate Copolymer), SEPIPLUS™ S (Hydroxyethyl Acrylate/Sodium Acryloyldimethyl Taurate Copolymer/Polyisobutene/PEG-7 Trimethylolpropane Coconut Ether), SEPIPLUS™ 265 (Ammonium Acrylate/Acrylamide Copolymer/Polyisobutene/Polysorbate 20), SEPIPLUS™ 400 (Polyacrylate-13/Polyisobutene/Polysorbate 20), SEPIGEL™ 305 (Polyacrylamide/C 13-14 Isoparaffin/Laureth-7), SIMULGEL™ A (Ammonium Polyacrylate/Isohexadecane/PEG-40 Castor Oil), SIMULGEL™ EG (Sodium Acrylate/Sodium Acryloyldimethyl Taurate Copolymer/Isohexadecane/Polysorbate 80), SIMULGEL™ EPG (Sodium Acrylate/Sodium Acryloyldimethyl Taurate Copolymer/Polyisobutene/Caprylyl Capryl Glucoside), SIMULGEL™ FL (Hydroxyethyl Acrylate/Sodium Acryloyldimethyl Taurate Copolymer/Isohexadecane/Polysorbate 60), SIMULGEL™ INS 100 (Hydroxyethyl Acrylate/Sodium Acryloyldimethyl Taurate Copolymer/Isohexadecane/Polysorbate 60), SIMULGEL™ SMS 88 (Sodium Acrylate Acryloyldimethyl Taurate/Dimethyacrylamide Crosspolymer/Isohexadecane/Polysorbate 60), SIMULGEL™ NS (Hydroxyethyl Acrylate/Sodium Acryloyldimethyl Taurate Copolymer/Squalane/Polysorbate 60), SIMULGEL™ 600 (Acrylamide/Sodium Acryloyldimethyl Taurate Copolymer/Isohexadecane/Polysorbate 80),
ARISTOFELX® AVC (Ammonium Acryloyldimthyltaurate/VP Copolymer),
ARISTOFELX® AVS (Sodium Acryloyldimethyltaurate/VP Copolymer),
ARISTOFELX® BLV (Ammonium Acryloyldimethyltaurate/Beheneth-25 Methacrylate Crosspolymer), and
ARISTOFELX® HMB (Ammonium Acryloyldimethyltaurate/Beheneth-25 Methacrylate Crosspolymer).

EXAMPLES

The following examples further describe and demonstrate the present invention. The examples are given solely for the purpose of illustration and are not to be construed as limitations of the present invention as many variations thereof are possible without departing from the spirit and scope of the invention. All of these examples can be made via the following general process, which one skilled in the art will be able to alter to incorporate available equipment.

SPF 50 Compositions

Examples 1-8

The following is a description of the manufacture of compositions according to the present invention having an SPF of 50. Other compositions may be made in a similar manner, and suggested phases and ranges of the amounts of each ingredient are set forth in TABLE 3.

The ingredients of Phase B, Phase C, Phase D and Phase E were prepared in separate suitable containers.

In a primary one liter beaker, water is added and homo mixing initiated with a Greerco Homogenizer. EDTA was added to the water, followed by the addition of ½ of the premix of Phase D to the beaker. UltraThix was sprinkled in to the beaker and the temperature in the beaker was maintained at 75° C. Phase B was heated to 80° C. in a separate container and Phase C was added to it. The mixture containing Phase B and Phase C was added to the beaker that contains Phase A. The remaining premix of Phase D is added to the beaker. The entire mixture in the main beaker was cooled to 40° C. and Phase E was added. The mixing continued until the emulsion had cooled to 30° C.

TABLE 3

| Ingredients | Examples | | | | | | | |
|---|---|---|---|---|---|---|---|---|
| | 1 % W/W | 2 % W/W | 3 % W/W | 4 % W/W | 5 % W/W | 6 % W/W | 7 % W/W | 8 % W/W |
| Phase A | | | | | | | | |
| Deionized water | 63.80 | 62.30 | 61.85 | 60.35 | 59.60 | 58.10 | 58.60 | 57.10 |
| Disodium EDTA | 0.10 | 0.10 | 0.10 | 0.10 | 0.10 | 0.10 | 0.10 | 0.10 |
| Arcylic acid/VP crosspolymer (Ultrathix P-100) | 0.50 | 0.50 | 0.50 | 0.50 | 0.50 | 0.50 | 0.50 | 0.50 |
| Phase B (oil phase) | | | | | | | | |
| Homosalate | 10.00 | 10.00 | 15.00 | 15.00 | 10.00 | 10.00 | 13.00 | 13.00 |
| Octisalate(Escalol 587) | 5.00 | 5.00 | 5.00 | 5.00 | 5.00 | 5.00 | 5.00 | 5.00 |
| Avobenzone(Escalol 517) | 3.00 | 3.00 | 1.50 | 1.50 | 3.00 | 3.00 | 3.00 | 3.00 |
| Oxybenzone (Escalol 567) | 6.00 | 6.00 | 6.00 | 6.00 | 6.00 | 6.00 | 6.00 | 6.00 |
| Octocrylene (Escalol 597) | 2.80 | 2.80 | 1.25 | 1.25 | 7.00 | 7.00 | 5.00 | 5.00 |
| Diisopropyl Adipate | 2.00 | 2.00 | 2.00 | 2.00 | 2.00 | 2.00 | 2.00 | 2.00 |
| Isocetyl Alcohol | 1.00 | 1.00 | 1.00 | 1.00 | 1.00 | 1.00 | 1.00 | 1.00 |
| Lauryl Lactate | 2.00 | 2.00 | 2.00 | 2.00 | 2.00 | 2.00 | 2.00 | 2.00 |
| Phase C | | | | | | | | |
| Gylceryl stearate (HLB = 3.8) | 0.50 | 2.00 | 0.50 | 2.00 | 0.50 | 2.00 | 0.50 | 2.00 |

TABLE 3-continued

| | Examples | | | | | | | |
|---|---|---|---|---|---|---|---|---|
| Ingredients | 1 % W/W | 2 % W/W | 3 % W/W | 4 % W/W | 5 % W/W | 6 % W/W | 7 % W/W | 8 % W/W |
| Phase D | | | | | | | | |
| Deionized water | 2.00 | 2.00 | 2.00 | 2.00 | 2.00 | 2.00 | 2.00 | 2.00 |
| TEA | 0.30 | 0.30 | 0.30 | 0.30 | 0.30 | 0.30 | 0.30 | 0.30 |
| Phase E | | | | | | | | |
| Germaben II E | 1.00 | 1.00 | 1.00 | 1.00 | 1.00 | 1.00 | 1.00 | 1.00 |
| Total (%) | 100.00 | 100.00 | 100.00 | 100.00 | 100.00 | 100.00 | 100.00 | 100.00 |

Examples 9-12

The following is a description of the manufacture of compositions according to the present invention having an SPF of 50. Other compositions may be made in a similar manner, and suggested phases and ranges of the amounts of each ingredient are set forth in TABLE 4.

The ingredients of Phase B, Phase C, and Phase D were prepared in separate suitable containers.

In a primary one liter beaker, water is added and homo mixing initiated with a Greerco Homogenizer. EDTA was added to the water, followed by the addition of ½ of the premix of Phase C to the beaker. Carbomer (Carbomer 940) was sprinkled in to the beaker and the temperature in the beaker was maintained at 60° C. Phase B was heated to 60° C. and Phase C was added to the beaker that contains Phase A. The remaining premix of Phase C is added to the beaker. The entire mixture in the main beaker was cooled to 40° C. and Phase D was added. The mixing continued until the emulsion had cooled to 30° C.

TABLE 4

| | Example | | | |
|---|---|---|---|---|
| Ingredients | 9 % W/W | 10 % W/W | 11 % W/W | 12 % W/W |
| Phase A | | | | |
| Deionized water | 65.50 | 61.30 | 60.30 | 63.55 |
| Disodium EDTA | 0.10 | 0.10 | 0.10 | 0.10 |
| Carbomer (Carbomer 940) | 0.30 | 0.30 | 0.30 | 0.30 |
| Phase B (oil phase) | | | | |
| Homosalate | 10.0 | 10.00 | 13.0 | 15.0 |
| Octisalate(Escalol 587) | 5.00 | 5.00 | 5.00 | 5.00 |
| Avobenzone(Escalol 517) | 3.00 | 3.00 | 3.00 | 1.50 |
| Oxybenzone (Escalol 567) | 6.00 | 6.00 | 6.00 | 6.00 |
| Octocrylene (Escalol 597) | 2.80 | 7.00 | 5.00 | 1.25 |
| Gylceryl stearate (HLB = 3.8) | 1.20 | 1.20 | 1.20 | 1.20 |
| Behenyl Alcohol | 1.20 | 1.20 | 1.20 | 1.20 |
| Cetyl Alcohol | 1.60 | 1.60 | 1.60 | |
| Phase C | | | | |
| Deionized water | 2.00 | 2.00 | 2.00 | 2.00 |
| TEA | 0.30 | 0.30 | 0.30 | 0.30 |
| Phase D | | | | |
| Germaben II E | 1.00 | 1.00 | 1.00 | 1.00 |
| Total (%) | 100.00 | 100.00 | 100.00 | 100.00 |

Examples 13-16

The following is a description of the manufacture of compositions according to the present invention having an SPF of 50. Other compositions may be made in a similar manner, and suggested phases and ranges of the amounts of each ingredient are set forth in TABLE 5.

The ingredients of Phase B, Phase C, and Phase D were prepared in separate suitable containers.

In a primary one liter beaker, water is added and homo mixing initiated with a Greerco Homogenizer. To the beaker 0.1% RapiThix A-100 was added. RapiThix A-100 was sprinkled in to the beaker until the entire mixture was hydrated and the temperature of mixture was maintained at 70-75° C. The mixture in the beaker was heated to 80° C. and Phase A was added to the beaker. The mixing continued until the emulsion mixture had reached 40-45° C. and Phase C was added. The mixing continued until the emulsion had cooled to 30° C.

TABLE 5

| | Example | | | |
|---|---|---|---|---|
| Ingredients | 13 % W/W | 14 % W/W | 15 % W/W | 16 % W/W |
| Phase A | | | | |
| Deionized water | 67.70 | 63.50 | 62.5 | 65.75 |
| RapiThix A-100 | 0.10 | 0.10 | 0.10 | 0.10 |
| Phase B (oil phase) | | | | |
| Homosalate | 10.00 | 10.00 | 13.00 | 15.00 |
| Octisalate(Escalol 587) | 5.00 | 5.00 | 5.00 | 5.00 |
| Avobenzone(Escalol 517) | 3.00 | 3.00 | 3.00 | 1.50 |
| Oxybenzone (Escalol 567) | 6.00 | 6.00 | 6.00 | 6.00 |
| Octocrylene (Escalol 597) | 2.80 | 7.00 | 5.00 | 1.25 |
| Gylceryl stearate (HLB = 3.8) | 1.20 | 1.20 | 1.20 | 1.20 |
| Behenyl Alcohol | 1.20 | 1.20 | 1.20 | 1.20 |
| Cetyl Alcohol | 1.60 | 1.60 | 1.60 | 1.60 |
| Phase C | | | | |
| RapiThix A-100 | 0.40 | 0.40 | 0.40 | 0.40 |
| Phase D | | | | |
| Germaben II E | 1.00 | 1.00 | 1.00 | 1.00 |
| Total (%) | 100.00 | 100.00 | 100.00 | 100.00 |

SPF 30 Compositions

Examples 17-20

The following is a description of the manufacture of compositions according to the present invention having an SPF of 30. Other compositions may be made in a similar manner, and suggested phases and ranges of the amounts of each ingredient are set forth in TABLE 6.

The ingredients of Phase B, Phase C, Phase D and Phase E were prepared in separate suitable containers.

In a primary one liter beaker, water is added and homo mixing initiated with a Greerco Homogenizer. EDTA was added to the water, followed by the addition of ½ of the premix of Phase D to the beaker. UltraThix was sprinkled in to the beaker and the temperature in the beaker was maintained at 75° C. Phase B was heated to 80° C. in a separate container and Phase C was added to it. The mixture containing Phase B and Phase C was added to the beaker that contains Phase A. The remaining premix of Phase D is added in to the beaker. The entire mixture in the main beaker was cooled to 40° C. and Phase E was added. The mixing continued until the emulsion had cooled to 30° C.

TABLE 6

| | Example | | | |
|---|---|---|---|---|
| Ingredients | 17 % W/W | 18 % W/W | 19 % W/W | 20 % W/W |
| Phase A | | | | |
| Deionized water | 66.10 | 64.60 | 64.6 | 63.10 |
| disodium EDTA | 0.10 | 0.10 | 0.10 | 0.10 |
| Arcylic acid/VP crosspolymer (Ultrathix P-100) | 0.50 | 0.50 | 0.50 | 0.50 |
| Phase B (oil phase) | | | | |
| Homosalate | 7.00 | 7.00 | 13.00 | 13.00 |
| Octisalate(Escalol 587) | 5.00 | 5.00 | 5.00 | 5.00 |
| Avobenzone(Escalol 517) | 2.00 | 2.00 | 2.00 | 2.00 |
| Oxybenzone (Escalol 567) | 3.00 | 3.00 | 4.00 | 4.00 |
| Octocrylene (Escalol 597) | | | 2.00 | 2.00 |
| Octinoxate (Escalol 557) | 7.50 | 7.50 | | |
| Diisopropyl Adipate | 2.00 | 2.00 | 2.00 | 2.00 |
| Isocetyl Alcohol | 1.00 | 1.00 | 1.00 | 1.00 |
| Lauryl Lactate | 2.00 | 2.00 | 2.00 | 2.00 |
| Phase C | | | | |
| Gylceryl stearate (HLB = 3.8) | 0.50 | 2.00 | 0.50 | 2.00 |
| Phase D | | | | |
| Deionized water | 2.00 | 2.00 | 2.00 | 2.00 |
| TEA | 0.30 | 0.30 | 0.30 | 0.30 |
| Phase E | | | | |
| Germaben II E | 1.00 | 1.00 | 1.00 | 1.00 |
| Total (%) | 100.00 | 100.00 | 100.00 | 100.00 |

Examples 21-22

The following is a description of the manufacture of compositions according to the present invention having an SPF of 30. Other compositions may be made in a similar manner, and suggested phases and ranges of the amounts of each ingredient are set forth in TABLE 7.

The ingredients of Phase B, Phase C, and Phase D were prepared in separate suitable containers.

In a primary one liter beaker, water is added and initiated homo mixing with a Greerco Homogenizer. EDTA was added to the water, followed by the addition of ½ of the premix of Phase C to the beaker. Carbomer (Carbomer 940) was sprinkled in to the beaker and the temperature in the beaker was maintained at 60° C. Phase B was heated to 60° C. and Phase C was added to the beaker that contains Phase A. The remaining premix of Phase C is added to the beaker. The entire mixture in the main beaker was cooled to 40° C. and added Phase D. The mixing continued until the emulsion had cooled to 30° C.

TABLE 7

| | Example | |
|---|---|---|
| Ingredients | 21 % W/W | 22 % W/W |
| Phase A | | |
| Deionized water | 67.8 | 66.3 |
| disodium EDTA | 0.10 | 0.10 |
| Carbomer (Carbomer 940) | 0.30 | 0.30 |
| Phase B (oil phase) | | |
| Homosalate | 7.00 | 13 |
| Octisalate(Escalol 587) | 5.00 | 5 |
| Avobenzone(Escalol 517) | 2.00 | 2 |
| Oxybenzone (Escalol 567) | 3.00 | 4 |
| Octocrylene (Escalol 597) | | 2 |
| Octinoxate (Escalol 557) | 7.5 | |
| Gylceryl stearate (HLB = 3.8) | 1.20 | 1.20 |
| Behenyl Alcohol | 1.20 | 1.20 |
| Cetyl Alcohol | 1.60 | 1.60 |
| Phase C | | |
| Deionized water | 2.00 | 2.00 |
| TEA | 0.30 | 0.30 |
| Phase D | | |
| Germaben II E | 1.00 | 1.00 |
| Total (%) | 100.00 | 100.00 |

Examples 23-24

The following is a description of the manufacture of compositions according to the present invention having an SPF of 30. Other compositions may be made in a similar manner, and suggested phases and ranges of the amounts of each ingredient are set forth in Table 8.

The ingredients of Phase B, Phase C, and Phase D were prepared in separate suitable containers.

In a primary one liter beaker, water is added and homo mixing initiated with a Greerco Homogenizer. To the beaker 0.1% RapiThix A-100 was added. RapiThix A-100 was sprinkled in to the beaker until the entire mixture was hydrated and the temperature of mixture was maintained at 70-75° C. The mixture in the beaker was heated to 80° C. and Phase A was added to the beaker. The mixing continued until the emulsion mixture had reached 40-45° C. and Phase C was added. The mixing continued until the emulsion had cooled to 30° C.

TABLE 8

| | Example | |
|---|---|---|
| Ingredients | 23 % W/W | 24 % W/W |
| Phase A | | |
| Deionized water | 70.0 | 68.5 |
| RapiThix A-100 | 0.10 | 0.10 |
| Phase B (oil phase) | | |
| Homosalate | 7.00 | 13.00 |
| Octisalate(Escalol 587) | 5.00 | 5.00 |
| Avobenzone(Escalol 517) | 2.00 | 2.00 |
| Oxybenzone (Escalol 567) | 3.00 | 4.00 |
| Octocrylene (Escalol 597) | | 2.00 |
| Octinoxate (Escalol 557) | 7.50 | |
| Gylceryl stearate (HLB = 3.8) | 1.20 | 1.20 |

TABLE 8-continued

| Ingredients | Example 23 % W/W | Example 24 % W/W |
|---|---|---|
| Behenyl Alcohol | 1.20 | 1.20 |
| Cetyl Alcohol | 1.60 | 1.60 |
| Phase C | | |
| RapiThix A-100 | 0.40 | 0.40 |
| Phase D | | |
| Germaben II E | 1.00 | 1.00 |
| Total (%) | 100.00 | 100.00 |

In a similar manner, the following compositions were prepared. The compositions exhibited little to no whitening when applied to the skin.

TABLE 9

| Phase | | Example 25 % w/w |
|---|---|---|
| A | Water | 59.60 |
| | Disodium EDTA | 0.10 |
| | Acrylic acid/VP crosspolymer (Ultrathix P-100) | 0.50 |
| B (oil phase) | Homosalate | 10.00 |
| | Octisalate (Escalol 587) | 5.00 |
| | Avobenzone (Escalol 517) | 3.00 |
| | Oxybenzone (Escalol 567) | 6.00 |
| | Octocrylene (Escalol 597) | 7.00 |
| | Diisopropyl Adipate (Cer 230) | 2.00 |
| | Isocetyl Alcohol (Cer ICA) | 1.00 |
| | Lauryl Lactate (Cer 31) | 2.00 |
| C | Glyceryl dilaurate (HLB = 4) | 0.50 |
| D | Deionized water | 2.00 |
| | TEA | 0.30 |
| E | Germaben II E | 1.00 |
| | Total | 100.00 |

TABLE 10

| Ingredients | Example 26 % W/W | Example 27 % W/W | Example 28 % W/W | Example 29 % W/W |
|---|---|---|---|---|
| Phase A | | | | |
| Deionized water | 66.05% | 64.55% | 64.55% | 63.05% |
| disodium EDTA | 0.10% | 0.10% | 0.10% | 0.10% |
| Arcylic acid/VP crosspolymer (Ultrathix P-100) | 0.50% | 0.50% | 0.50% | 0.50% |
| Phase B (oil phase) | | | | |
| Homosalate | 7.00% | 13.0% | 7.00% | 13.0% |
| Octisalate(Escalol 587) | 5.00% | 5.00% | 5.00% | 5.00% |
| Avobenzone(Escalol 517) | 2.00% | 2.00% | 2.00% | 2.00% |
| Oxybenzone (Escalol 567 | 3.00% | 4.00% | 3.00% | 4.00% |
| Octocrylene (Escalol 597) | | 2.00% | | 2.00% |
| Octinoxate (Escalol 557) | 7.50% | | 7.50% | |
| Diisopropyl Adipate | 2.00% | 2.00% | 2.00% | 2.00% |
| Isocetyl Alcohol | 1.00% | 1.00% | 1.00% | 1.00% |
| Lauryl Lactate | 2.00% | 2.00% | 2.00% | 2.00% |
| Phase C | | | | |
| Gylceryl stearate (HLB = 3.8) | 0.50% | 0.50% | 2.00% | 2.00% |
| Sucrose Stearate (HLB = 16) | 0.05% | 0.05% | 0.05% | 0.05% |
| Phase D | | | | |
| Deionized water | 2.00% | 2.00% | 2.00% | 2.00% |
| TEA | 0.30% | 0.30% | 0.30% | 0.30% |
| Phase E | | | | |
| Germaben II E | 1.00% | 1.00% | 1.00% | 1.00% |
| Total | 100.00% | 100.00% | 100.00% | 100.00% |

The compositions of the present invention were surprisingly found capable of providing little to no whitening when applied to wet skin.

In particular embodiments, the sunscreen composition of present invention can comprise one or more additional film forming and/or waterproofing agents and the like.

In particular embodiments, the film forming agent can be selected from polyvinylpyrrolidone polymers. Particularly preferred are copolymers of polyvinylpyrrolidone such as polyvinylpyrrolidone/hexadecen copolymer (Antaron V216), polyvinylpyrrolidone/eicosan copolymer (Antaron V220), butylated polyvinylpyrrolidone (Antaraon P-904) as well as the tricontanyl polyvinylpyrrolidone (Antaron WP-660) which are available from Ashland Inc. Furthermore, Ganex P-904 (poly(butylated vinylpyrrolidone)), Ganex V-216 (vinylpyrrolidone and hexadecene copolymer), Ganex V-220 (vinylpyrrolidone and eicosene copolymer), and Ganex WP-660 (vinyl pyrrolidone and 1-triacontane copolymer), all available from Ashland Inc and Stearoxy Dimethicone (Abil Wax 2434), Behenoxy Dimethicone (Abil Wax 2440), Stearyl Dimethicone (Abil Wax 9800), Cetyl Dimethicone (Abil Wax 9801, Abil Wax 9814, Abil Wax 9840), C24-28 Alkyl Methicone (Abil Wax 9810 P), Acry Iates/C 12-22 Alkyl Methacrylate Copolymer (Allianz OPT available from Ashland Inc) are particularly useful.

In particular embodiments, the sunscreen composition of present invention further comprise one or more additional components conventionally used in sunscreen compositions such as skin-feel additives, pH adjusters, chelating agents, anti-aging agents, exfoliating agents, treatment agents, fragrances, emollients, liquid carriers, waxes, conditioners, surfactants, rheology modifiers, lubricants, diluents, humectants, anti-oxidants, preservatives, antibiotics, viscosity synergists, clarity synergists, antioxidants, anti-aging ingredients, moisturizing agents, preservatives and blends thereof.

While the invention has been described in detail with particular reference to preferred embodiments featuring an oil-in-water emulsion composition containing a UV active, it is believed that the invention can be practiced in conjunction with oil-in-water emulsion compositions featuring cosmetic and medicinal products to be applied to the skin.

The invention has been described in detail with particular reference to preferred embodiments thereof, but it will be understood that modifications and variations can be effected within the spirit and scope of the invention.

We claim:
1. An oil-in-water emulsion wet-skin sunscreen composition consisting of:
    (a) one or more UV actives,
    (b) 0.1% w/w to about 5% w/w of a first emulsifier having an HLB value less than 5, wherein the first emulsifier may be comprised of one emulsifier compound or a combination of emulsifier compounds,
    (c) a second emulsifier having an HLB value greater than 5, wherein the second emulsifier is present in an amount from about 0.05% w/w to about 0.2% w/w of said composition, and may be comprised of one emulsifier compound or a combination of emulsifier compounds;
    (d) one or more film forming and/or water proofing agents selected from the group consisting of poly (butylated vinylpyrrolidone), vinylpyrrolidone and hexadecene copolymer, vinylpyrrolidone and eicosene copolymer, vinyl pyrrolidone and 1-triacontane copolymer, acrylates/$C_{12}$-$C_{22}$ alkylmethacrylate copolymer, acrylic acid/vinylpyrrolidone crosspolymer, and blends thereof,
    (e) one or more ingredients selected from the group consisting of skin-feel additives, pH adjusters, chelating agents, exfoliating agents, treatment agents, fragrances, emollients, liquid carriers, waxes, conditioners, surfactants, rheology modifiers, lubricants, diluents, humectants, antibiotics, viscosity synergists, clarity synergists, antioxidants, anti-aging ingredients, moisturizing agents, preservatives and blends thereof, and
    (f) water;
    wherein said oil-in-water wet-skin sunscreen composition is free of an emulsifiable polymer, which is defined as a polymer containing hydrophobic chains and causing flaking and/or whitening upon application to wet skin;
    wherein the first emulsifier is selected from the group consisting of glycol distearate, sorbitan trioleate, glycol stearate, sorbitan sesquioleate, glyceryl stearate, glyceryl dilaurate, lecithin, sorbitan oleate, sorbitan stearate, sorbitan isostearate, oleth-2 and steareth-2, and blends thereof; and
    wherein the second emulsifier is selected from the group consisting of calcium stearoyl lactylate, glyceryl laurate, ceteth-2, PEG-30 dipolyhydroxystearate, glyceryl stearate SE, PEG-4 dilaurate, sorbitan stearate (and) sucrose cocoate, methyl glucose sesquistearate, sucrose stearate, PEG-10 sunflower glycerides, sodium stearoyl lactylate, sorbitan laurate, PEG-40 sorbitan peroleate, lecithin, laureth-4, PEG-7 glyceryl cocoate, PEG-20 almond glycerides, linoleamide DEA, PEG-25 hydrogenated castor oil, cetearyl glucoside, polysorbate 85, glyceryl stearate (and) PEG-100 stearate, stearamide MEA, oleth-10/polyoxyl 10 oleyl ether NF, oleth-10, oleth-20, ceteth-10, PEG-8 laurate, cocamide MEA, polysorbate 60, PEG-60 almond glycerides, isosteareth-20, lauramide DEA, PEG-30 dipolyhydroxystearate, polysorbate 80, PEG-20 methyl glucose sesquistearate, ceteareth-20, oleth-20, steareth-21, ceteth-20, isoceteth-20, polysorbate 20, laureth-23, PEG-100 stearate, PEG-80 sorbitan laurate and blends thereof.

2. The composition of claim 1 wherein said one or more UV actives is selected from the group consisting of UV-A and/or UV-B actives.

3. The composition of claim 1, wherein the second emulsifier is selected from the group consisting of PEG-4 dilaurate, sorbitan stearate (and) sucrose cocoate, methyl glucose sesquistearate, PEG-10 sunflower glycerides, sodium stearoyl lactylate, sorbitan laurate, and blends thereof.

4. The composition of claim 1, wherein said one or more UV actives is selected from the group consisting of: methoxydibenzoylmethane; octyl salicylate; pentyl dimethyl PABA; octyl dimethyl PABA; benzophenone-1; benzophenone-6; 2-(2H-benzotriazole-2-yl)-4,6-di-tert-pentylphenol; ethyl-2-cyano-3,3-diphenylacrylate; homomethyl salicylate (homosalate); bis-ethylhexyloxyphenol methoxyphenyl triazine; methyl-(1,2,2,6,6-pentamethyl-4-piperidyl)-sebacate; 2-(2H-benzotriazole-2-yl)-4-methylphenol; diethylhexyl butamido triazone; amyl dimethyl PABA; 4,6-bis (octylthiomethyl)-o-cresol; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol;2-hydroxy-4-octyloxybenzophenone; benzophenone-2; diisopropyl methylcinnamate; PEG-25 PABA; 2-(1,1-dimethylethyl)-6-[[3-(1,1-demethylethyl)-2-hydroxy-5-methylphenyl]methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis [3-(3,5-di-tert-butyl-4-hydroxyphenylpropionamide)]; pentaerythritol tetrakis [3-(3,5-di-tert-butyl-4-hydroxyphenyl)propionate]; 2,6-di-tert-butyl-4-[4,6-bis(octylthio)-1,3,5-triazin-2-ylaminolphenol; 2-(2H-benzotriazole-2-yl)-4,6-bis(1-methyl-1-phenylethyl) phenol; trolamine salicylate; diethylanolamine p-methoxycinnamate; polysilicone-15; 4-methylbenzylidene camphor; bisoctrizole; N-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor; glyceryl ethylhexanoate dimethoxycinnamate; 1,3-bis-[(2'-cyano-3',3'-diphenylacryloyl)oxy}-2,2-bis-[(2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylendiamine; benzophenone-8; ethyl-4-bis(hydroxypropyl)aminobenzoate; 6-tert-butyl-2-(5-chloro-2H-benzotriazole-2-yl)-4-methylphenol; p-aminobenzoic acid; 3,3',3", 5,5',5"-hexa-tert-butyl-α-α'-α"-(mesitylene-2,4,6-triyl)tri-p-cresol;
lawsone with dihydroxyacetone; benzophenone-9; benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor; terephthalylidene dicamphor sulfonic acid; camphor benzalkonium methosulfate; bisdisulizole disodium; etocrylene; ferulic acid;2-(2H-benzotriazole-2-yl)-4-(1,1,3,3-tetramethylbutyl)-phenol; 4,6-bis(dodecylthiomethyl)-o-cresol; β-2-glucopyranoxy propyl hydroxy benzophenone; phenylbenzimidazole sulfonic acid; benzophenone-3; diethylamine hydroxybenzoyl hexylbenzoate; 3',3"-diphenylacryloyl) oxy]methyl}-propane; ethylhexyl p-methoxycinnamate, and blends thereof.

5. The composition of claim 4, wherein said one or more UV actives is selected from the group consisting of homomenthyl salicylate (homosalate), octisalate, avobenzone, oxybenzone, octocrylene, and blends thereof.

6. The composition of claim 1, wherein said one or more UV actives is present in an amount of 0.1 to 50% w/w of the total composition.

* * * * *